US010327661B1

(12) United States Patent
Iasemidis et al.

(10) Patent No.: US 10,327,661 B1
(45) Date of Patent: Jun. 25, 2019

(54) BIOMARKERS FOR DETERMINING SUSCEPTIBILITY TO SUDEP

(71) Applicants: Leonidas D. Iasemidis, Choudrant, LA (US); Ioannis Vlachos, Ruston, LA (US); Albert Edward Glasscock, Shreveport, LA (US)

(72) Inventors: Leonidas D. Iasemidis, Choudrant, LA (US); Ioannis Vlachos, Ruston, LA (US); Albert Edward Glasscock, Shreveport, LA (US)

(73) Assignees: Louisiana Tech Research Corporation, Ruston, LA (US); Board of Supervisors of Louisiana State University and Agricultural and Mechanical College, Shreveport, LA (US)

(*) Notice: Subject to any disclaimer, the term of this patent is extended or adjusted under 35 U.S.C. 154(b) by 289 days.

(21) Appl. No.: 14/804,658

(22) Filed: Jul. 21, 2015

Related U.S. Application Data (60) Provisional application No. 62/027,521, filed on Jul. 22, 2014.

(51) Int. Cl.
| A61B 5/0452 | (2006.01) |
| A61B 5/024 | (2006.01) |
| A61B 5/00 | (2006.01) |
| A61B 5/0476 | (2006.01) |
| A61B 5/0456 | (2006.01) |

(52) U.S. Cl.
CPC ........ *A61B 5/0452* (2013.01); *A61B 5/02405* (2013.01); *A61B 5/0456* (2013.01); *A61B 5/0476* (2013.01); *A61B 5/4094* (2013.01); *A61B 5/726* (2013.01); *A61B 5/7257* (2013.01)

(58) Field of Classification Search
CPC ... A61B 5/0006; A61B 5/0402; A61B 5/0468; A61B 5/4094; A61B 5/7275
See application file for complete search history.

(56) References Cited

U.S. PATENT DOCUMENTS

| 7,373,199 B2 | 5/2008 | Sackellares et al. |
| 8,562,524 B2 | 10/2013 | Osorio |
| 8,761,868 B2 | 6/2014 | Giftakis et al. |
(Continued)

FOREIGN PATENT DOCUMENTS

WO 01/21067 A1 3/2001

OTHER PUBLICATIONS

Balamurugan et al., Perceived trigger factors of seizures in persons with epilepsy, All India Institute of Medical Sciences, Seizure 22, pp. 743-747, Mar. 2013.*
(Continued)

*Primary Examiner* — Puya Agahi
(74) *Attorney, Agent, or Firm* — Jones Walker LLP (57) ABSTRACT

A method for determining an increased risk of death of a patient includes receiving ECG data of the patient generated during a first time period; receiving EEG data of the patient generated during the first time period; composing a feature of the ECG data and a feature of the EEG data over a common time frame and determining a statistical measure of association between the ECG data and the EEG data; and determining whether the degree of association exceeds a predetermined threshold, thereby indicating whether an increased risk is present.

16 Claims, 6 Drawing Sheets

(56) References Cited

U.S. PATENT DOCUMENTS

| | | | |
|---|---|---|---|
| 8,795,173 B2 | 8/2014 | Poh et al. | |
| 2007/0150025 A1* | 6/2007 | Dilorenzo | A61B 5/0476 607/45 |
| 2008/0208074 A1* | 8/2008 | Snyder | A61B 5/0476 600/545 |
| 2009/0264952 A1 | 10/2009 | Jassemidis et al. | |
| 2010/0198289 A1 | 8/2010 | Kameli et al. | |
| 2012/0215462 A1* | 8/2012 | Goode, Jr. | A61B 5/14532 702/19 |
| 2012/0298105 A1 | 11/2012 | Osorio | |
| 2013/0281797 A1 | 10/2013 | Sabesan | |
| 2014/0081090 A1* | 3/2014 | Picard | G06F 19/3418 600/301 |

OTHER PUBLICATIONS

Shannon, Claude Elwood. "A mathematical theory of communication." The Bell System Technical Journal, vol. XXVII, No. 3 (1948): 379-423.

Bendat, Julius S., and Allan G. Piersol. "Stationary Random Processes." Random Data: Analysis and Measurement Procedures, Fourth Edition (2012): 134-135.

Pan, Jiapu, and Willis J. Tompkins. "A real-time QRS detection algorithm." Biomedical Engineering, IEEE Transactions on 3 (1985): 230-236.

\* cited by examiner

| Example Phi (Φ) Coefficients |
|---|
| $ENTR_{ch1}$ vs. $ENTR_{Rpeak}$ |
| $ENTR_{ch2}$ vs. $ENTR_{RPEAK}$ |
| $ENTR_{ch1}$ vs. $ENTR_{PG}$ |
| $ENTR_{ch2}$ vs. $ENTR_{PG}$ |
| $C(\delta)$ vs. $M_{RR}$ |
| $C(B)$ vs. $M_{RR}$ |
| $C(\delta)$ vs. $M_{RPeak}$ |
| $C(\delta)$ vs. $IQR_{Rpeak}$ |
| $C(\delta)$ vs. $ENTR_{RR}$ |

| φ Coefficient | | | |
|---|---|---|---|
| Pairs of measures | Kcna1 -/- Scn2a +/- | Kcna1 -/- | p-value of t-test on φ |
| $C(\delta) - M_{Rpeak}$ | 0.20 | 0.05 | 0.01 |
| $C(\delta) - IQR_{Rpeak}$ | 0.19 | 0.03 | 0.04 |
| $C(\delta) - ENT_{RR}$ | 0.14 | 0.02 | 0.01 |
| $C(\delta) - M_{RR}$ | 0.22 | 0.03 | 0.01 |
| $C(\beta) - M_{RR}$ | 0.23 | 0.04 | 0.02 |

BIOMARKERS FOR DETERMINING SUSCEPTIBILITY TO SUDEP

This application claims the benefit under 35 USC 119(e) of U.S. Provisional Application Ser. No. 62/027,521 file Jul. 22, 2014, which is incorporated by reference herein in its entirety.

I. BACKGROUND

This application relates to diagnosing and treating conditions which potentially lead to sudden death, normally from cardiorespiratory arrest, in persons who are not otherwise recognized as being at risk for imminent death. One form of this sudden death syndrome is sudden unexpected death in epilepsy (SUDEP). Prevention of SUDEP is complicated by the inability to accurately predict which patients are at risk. Many SUDEP risk factors have been proposed based on demographic parameters (e.g., early onset epilepsy, generalized tonic-clonic seizures, and male sex) and physiological parameters (e.g., heart rate variability and postictal EEG suppression). However, these risk factors have limited predictive value as many patients with low risk profiles still die of SUDEP while some patients with higher risk profiles do not. More reliable methods for determining which persons are at risk for SUDEP would provide significant live-saving benefits.

II. SUMMARY OF SELECTED EMBODIMENTS

One embodiment of the invention is a method for determining an increased risk of death of a patient. The method includes receiving ECG data of the patient generated during a first time period; receiving EEG data of the patient generated during the first time period; composing a feature of the ECG data and a feature of the EEG data over a common time frame and determining a statistical measure of association between the ECG data and the EEG data; and determining whether the degree of association exceeds a predetermined threshold, thereby indicating whether an increased risk is present.

Another embodiment is a system for determining an increased risk of death of a patient. The system includes an ECG monitor configured to generate ECG data from the patient when connected to the ECG monitor; an EEG monitor configured to generate EEG data from the patient when connected to the EEG monitor; and a processor. The processor carries out the steps of receiving the ECG data of the patient generated during a first time period; receiving the EEG data of the patient generated during the first time period; composing a feature of the ECG data and a feature of the EEG data over a common time frame and determining a statistical measure of association between the ECG data and the EEG data; and determining whether the degree of association exceeds a predetermined threshold, thereby indicating whether an increased risk is present.

A further embodiment is software for determining in real-time an increased risk of death relating to a patient with a neurological disorder. The software stores instructions that, when executed by a processor, perform a method including the steps of: receiving ECG data of the patient generated during a first time period; receiving EEG data of the patient generated during the first time period; composing a feature of the ECG data and a feature of the EEG data over a common time frame and determining a statistical measure of association between the ECG data and the EEG data; and determining whether the degree of association exceeds a predetermined threshold, thereby indicating whether an increased risk is present.

IV. DETAILED DESCRIPTION OF SELECTED EMBODIMENTS

One embodiment of the invention is a method for determining an increased risk of death of a patient. Generally, the method includes recording electrocardiographic (ECG) data and electroencephalographic (EEG) data; extracting feature values from the recorded ECG and EEG data; determining a statistical measure of association between the ECG and EEG features; and determining whether the measure of association exceeds a predetermined threshold, thereby indicating whether an increased risk is present.

Figure 1:
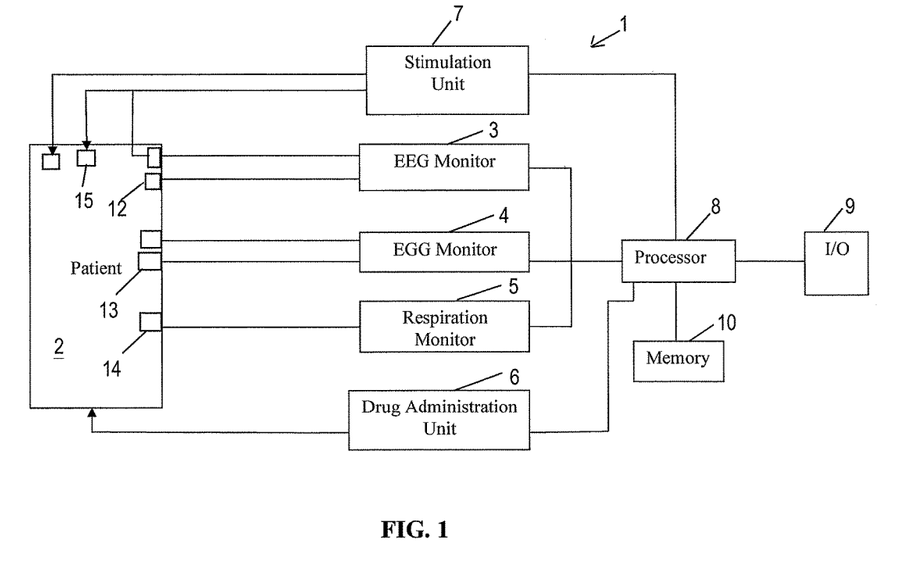
FIG. 1 is a component diagram of one system embodiment of the present invention.

FIG. 1 illustrates the components of one system for carrying out this method. This embodiment of system 1 for determining an increased risk of death generally comprises the EEG monitor 3, the ECG monitor 4, and the processor 8. Processor 8 will normally be accompanied by some type of memory 10 and some type of input/output (I/O) 9. As one example, I/O 9 may include a keypad (touchscreen) for inputting commands and some type of display/monitor for informing the user of results or the status of operation. FIG. 1 suggests how the EEG monitor 3 will have electrodes 12 connected to a patient 2 and ECG monitor 4 will have electrodes 13 connected to the patient. In certain embodiments, the system 1 may include a stimulation unit 7 and/or a drug administration unit 6, both of which will be described in more detail below. The system 1 may be of any conventional or future developed form implementing the claimed elements. For example, system 1 could include conventional EEG and ECG monitors in a hospital or doctor's office setting with a general purpose computer (e.g., personal computer, laptop or tablet) receiving the EEG/ECG data and performing the processing steps described herein. Alternatively, the components of the system could be smaller and utilize a special purpose computer such that the entire system is contained in a pouch worn by the patient. Still more futuristic embodiments may be miniaturized to the point that some or all of the components may be implanted within the patient's body. All such variations are within the scope of the present invention.

Figure 2:
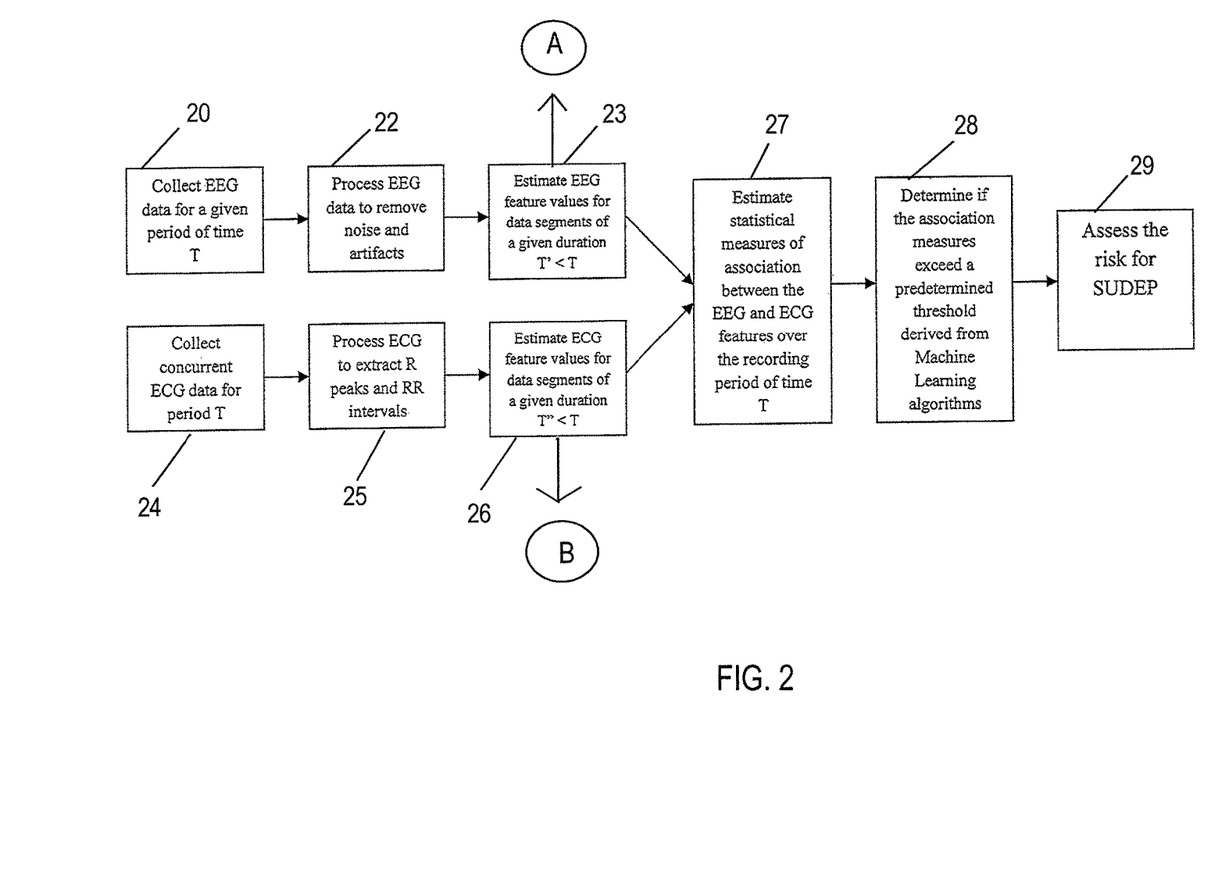
FIG. 2 is a general method flow chart for one embodiment of the invention.

FIG. 2 illustrates a flow chart for one embodiment of the method for determining an increased risk of death of a patient. In step 20, the EEG data is collected for a given period of time T in the range of 12 to 24 hours. However, certain embodiments may collect data for a period of time T less than one hour or more than 24 hours. In one example, the period of time T could be any period of time between one hour and 48 (or even more) hours. As is well known in the art, the EEG data may be recorded by an electrode montage of any number of channels, with each channel representing the difference of the electromagnetic potential between a particular electrode and a designated reference electrode. The number of electrodes may vary considerably, with two electrodes being the minimum and a more typical number being the International 10-20 system having 19 recording electrodes plus one reference electrode (thus 19 channels). Naturally, systems with more than 20 electrodes could also be employed.

Similarly in step 24 of FIG. 2, ECG data is collected. Normally the ECG data is collected for the same time period T as the EEG data. The raw ECG data and EEC data may not be collected over the exact same period of time, but for purposes of the FIG. 2 method, it is only the time period T over which the ECG and EEG data are concurrently recorded that is relevant. As is again known in the art, ECG data is a voltage versus time representation of the overall magnitude and direction of the heart's electrical depolarization at each moment throughout the cardiac cycle. A typical ECG tracing manifests a repeating cycle of three prominent electrical entities: a P wave (atrial depolarization), a QRS complex (ventricular depolarization) and a T wave (ventricular repolarization). Common ECG parameters of interest include the QRS complexes (e.g., such as detected by the Pan-Tompkins algorithm), the R peak values (i.e., the greatest amplitude of QRS complex's R wave), and the RR interval durations. The number of electrodes used to collect ECG data may vary, with the conventional 10 electrode (12 channel) system being a common example for many human applications.

Turning to step 22 of FIG. 2, the EEG data is processed (or pre-processed) to remove noise and artifacts. This pre-processing step might include, for example, signal amplification, filtering and digitization. In a preferred embodiment, filters, including a high pass filter with 0.1 to 1 Hz cutoff and a low pass filter with 70-200 Hz cutoff, are employed. Depending on the application and/or the signal recording environment, other filters may be employed. For instance, if the signals are being recorded in the vicinity of power lines or any electrical fixtures or appliances operating on a 60 Hz cycle, a 60 Hz notch filter or time varying digital filters may be employed. In many embodiments, the pre-processing step 22 results in the generation of a digital time series for each channel.

Next in step 23, the method makes an estimate of EEG "feature values" for a series of smaller duration successive segments taken from the EEG data. The extracted feature values from any signal, EEG or ECG, may be any numerical representation of a distinctive attribute or aspect (feature) of a signal estimated by mathematical analysis of the signal itself. Some nonlimiting examples of features include (i) Linear (time domain) features such as statistical moments (e.g., mean, standard deviation, Kurtosis, skewness), Modeling based (e.g., autoregressive modeling coefficients, Vector autoregressive modeling coefficients), Signal energy (e.g., Barlow parameters, Teager energy, Hjorth parameters), Correlation coefficients (e.g., Pearson product-moment correlation coefficient, Rank correlation); (ii) Linear (frequency domain) features such as power (e.g., spectral band power at specific frequencies/frequency bands, normalized spectral band power), Frequency (e.g., spectral edge frequency, median frequency), frequency-based Connectivity (e.g., coherence, directed transfer function, partial coherence, directed coherence, generalized partial directed coherence); and (iii) Non-linear features such as entropy based (e.g., Shannon entropy, approximate entropy, sample entropy, spectral entropy, mutual information, transfer entropy), Chaos theory based (e.g., Lyapunov exponents, correlation dimension, recurrence quantification analysis, dynamical entrainment, non-linear interdependence), Long range correlations (e.g., detrended fluctuation analysis, Hurst exponent), Algorithmic complexity (e.g., Lempel-Ziv complexity), and Cross-frequency coupling (e.g., phase synchronization, phase-amplitude coupling, bispectrum, bicoherence). In certain embodiments, the feature value are extracted entirely (or substantially entirely) from the EEG signal during a time period when a seizure is not occurring (e.g., not during pre-ictal, ictal, and post-ictal periods in the EEG data).

Figure 3A:
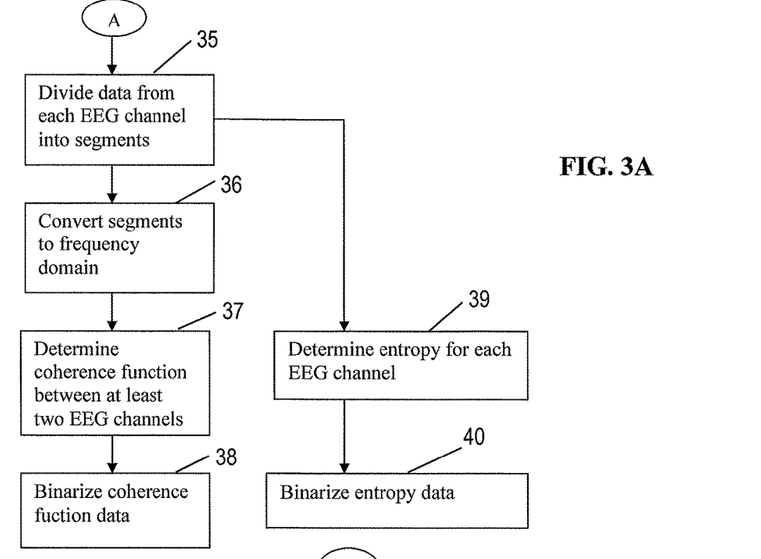
FIG. 3A is a flow chart showing one embodiment for determining EEG feature values.

FIG. 3A illustrates in more detail the derivation of two examples of feature values: coherence and entropy values. First in step 35, the EEG data from each channel over the time period T is divided into smaller duration segments (e.g., 10 s segments). In step 36, the signal within each segment is transformed into the frequency domain by a convention technique, e.g., a Fourier or Wavelet transform. Next (step 37) the coherence function of frequency between at least two channels is determined. In cases where there are many channels (e.g. 19), the coherence function may be determined between many different pairs of channels. Empirical studies are likely to suggest comparison of certain pairs of channels that are more indicative of relevant SUDEP characteristics than other pairs of channels. Coherence, as a feature from the frequency domain, reflects the similarity between components of two signals at a particular frequency. For two signals $x_i(t)$ and $x_j(t)$, the coherence function at frequency f between them is defined as:

$$C_{ij}(f) = \frac{|S_{ij}(f)|}{\sqrt{S_{ii}(f)S_{jj}(f)}},$$

where $S_{ii}(f), S_{jj}(f)$ are the individual power spectral densities of $x_i$ and $x_j$, and $S_{ij}(f)$ is their cross power spectral density at frequency f. The individual power spectral densities are estimated from the Fourier transform of the autocorrelation function of each signal, and the cross power spectral density is estimated as the Fourier transform of the crosscorrelation function between the two signals. By summing the coherence values within a specific frequency band $[f_1, f_2]$ the coherence value for a specific frequency band is obtained. See for example, J. S. Bendat, A. G. Piersol, *Random Data: Analysis and Measurement Procedures*, Wiley-Interscience, 1986, which is incorporated by reference herein, for discussion of coherence determinations. The frequency band can be one of the traditional EEG bands ($\delta$-band [0.5-3 Hz], $\theta$-band [3.5-7 Hz], $\alpha$-band [8-12 Hz], $\beta$-band [13-20 Hz], and $\gamma$-band [21-50 Hz]), or any other band empirically found to be useful in determining SUDEP risks.

In addition to the coherence function, step 39 estimates the entropy (in this case the Shannon entropy) from the time domain of one or more EEG channels. Shannon entropy is a measure of uncertainty that quantifies the degree of complexity of a signal. For a given signal x(t), the entropy is defined as:

$$H(x) = -\Sigma p(x)\ln(p(x)),$$

where p(x) is an estimate of the probability distribution function of the values a signal exhibits, and can be approximated by a histogram. See for example, C. E. Shannon, W. Weaver. *The Mathematical Theory of Communication*, Univ of Illinois Press, 1949. ISBN 0-252-72548-4, which is incorporated by reference herein. Once the coherence function and entropy are determined, steps 38 and 40 binarize the segments of these features in preparation for further processing steps described below.

Figure 3B:
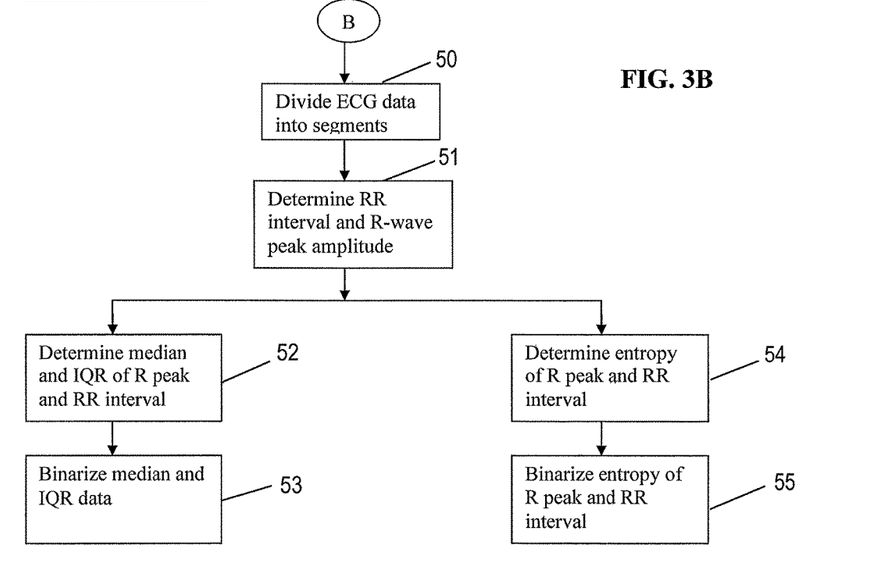
FIG. 3B is a flow chart showing one embodiment for determining ECG feature values.

Returning to FIG. 2 and treatment of ECG data, step 25 involves the extraction of ECG parameters such as R peaks and RR intervals. As suggested above, QRS complexes can be detected by one of many existing algorithms, e.g. the Pan-Tompkins algorithm (see J. Pan, W. J. Tompkins, "A Real-Time QRS Detection Algorithm," Biomedical Engineering, IEEE Transactions on, vol.BME-32, no.3, pp. 230, 236, March 1985, which is incorporated by reference herein). After the QRS detection is applied to a given segment of data, the RR interval durations and R peak values are extracted and treated as two distinct signals. In step 26, ECG feature values are estimated for the ECG segments over the same time periods as the EEG data. FIG. 3B shows in more detail the derivation of example ECG feature values; median, interquartile range (IQR), and entropy. In step 50, the ECG data is divided into shorter duration segments (e.g., 10 s as described above for EEG data). Next in step 51, the R-R interval and the R wave peak amplitude (Rpeak) is determined. In step 52, the median and the IQR of the R-R interval and the Rpeak is determined for each segment. The IQR is the difference between the 75% and 25% quartiles of the data set. Likewise, in step 54, the entropy of the R-R interval and the Rpeak is found. Thereafter, all of the feature values (median, IQR, and entropy) are binarized in steps 53 and 55.

Step 27 of FIG. 2 next suggests how statistical measures of association are estimated between the binarized feature values of the EEG and ECG data. As used herein, "statistical measures of association" may include any statistic that measures the strength and nature of the relationship between variables. Nonlimiting examples of statistical measures of association include (i) Chi Square based measures such as Phi, the contingency coefficient, and Cramer's V; (ii) Reduction in Error Measures based measures such as Asymmetric and Symmetric Lambda; (iii) Linear measures of correlation such as Pearson's product moment correlation and Spearman's rho; and (iv) nonlinear measure of correlation such as mutual information. As suggested in the example below and FIG. 7, one embodiment determines the Phi coefficient between (i) coherence in the EEG delta band, C($\delta$), and the Median Rpeak value, (ii) C($\delta$) and the IQR Rpeak value, (iii) C($\delta$) and RR Interval entropy, (iv) C($\delta$) and the RR Interval Median, and (v) C($\beta$) and the RR Interval Median. However, measures of association could be taken between many other feature values (e.g., see FIG. 4 for additional phi coefficient examples).

Figure 5:
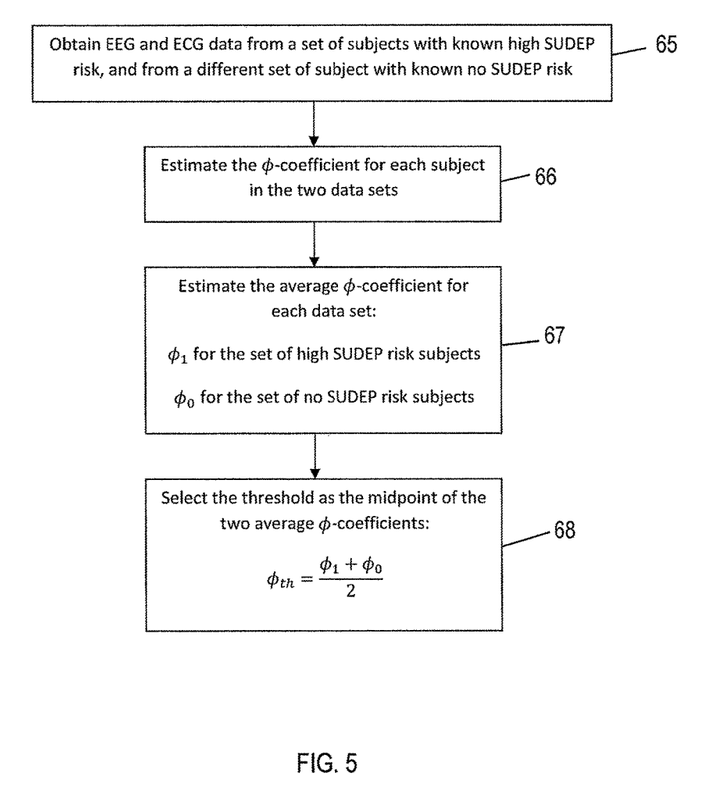
FIG. 5 is a flow chart showing the steps of a simple machine learning algorithm.
Figure 7:
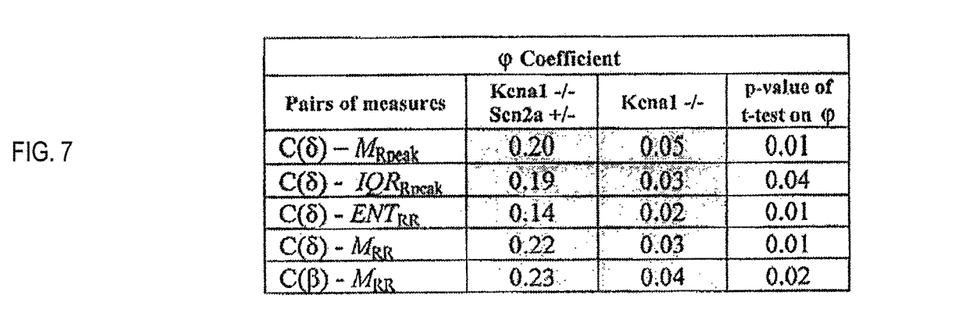
FIG. 7 is a chart of Phi coefficient values between example feature values.

Step 28 of FIG. 2 suggests how this method embodiment will determine whether the measures of associations exceed a predetermined threshold. The threshold may be determined in any number of different ways. For example, FIG. 7 shows the Phi coefficient for two different sets of genetically engineered mice. One set of mice exhibit symptoms analogous to SUDEP, while the other set of mice exhibit epileptic seizures that are usually non-lethal. In this simple example, the Phi coefficients between these two sets of mice suggest a reasonable threshold might be determined as 0.1. As suggested in step 28, this threshold would be used to assess the risk of SUDEP, i.e., Phi coefficients for the feature set which are above 0.1 suggest a high association between ECG and EEG and therefore a lower risk of SUDEP, while Phi coefficients below 0.1 suggest a higher risk for SUDEP. In certain embodiments, the threshold may be determined by a machine learning algorithm, with FIG. 5 suggesting a simple method example. In step 65 of FIG. 5, EEG and ECG data are obtained from one set of subjects with a known high SUDEP risk and from a different set of subjects known not to have a high SUDEP risk. Step 66 estimates the Phi coefficient for each subject in the two data sets. Next, step 67 estimates the average Phi coefficient for each data set, i.e., $\varphi_1$ for the set of high SUDEP risk subjects and $\varphi_2$ for the set of low SUDEP risk subjects. Finally, step 68 selects the threshold as the midpoint of the two average Phi coefficients.

In many preferred embodiments, the machine learning algorithm will be selected from the "supervised learning" category of algorithms, which in essence means that the threshold will be obtained from a large dataset with subjects/patients of known conditions. Exemplary supervised learning algorithms might include artificial neural networks (e.g., backpropagation, autoencoders, Hopfield networks, Boltzmann machines, etc.), Bayesian statistics (e.g., Bayesian network, Bayesian knowledge base), case-based reasoning, inductive logic programming, Gaussian process regression, learning vector quantization, logistic model tree, decision trees, support vector machines, etc.

Figure 3C:
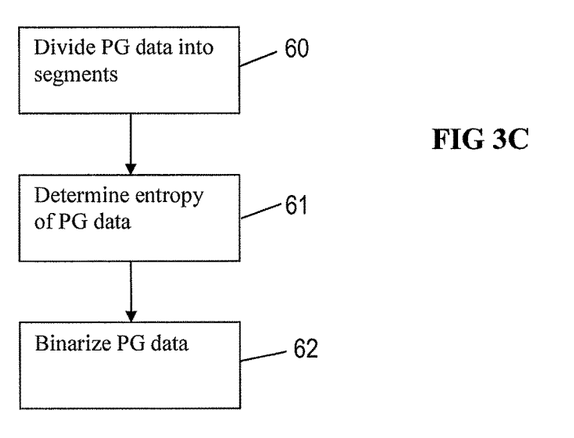
FIG. 3C is a flow chart showing one embodiment for determining PG feature values.
Figure 4:
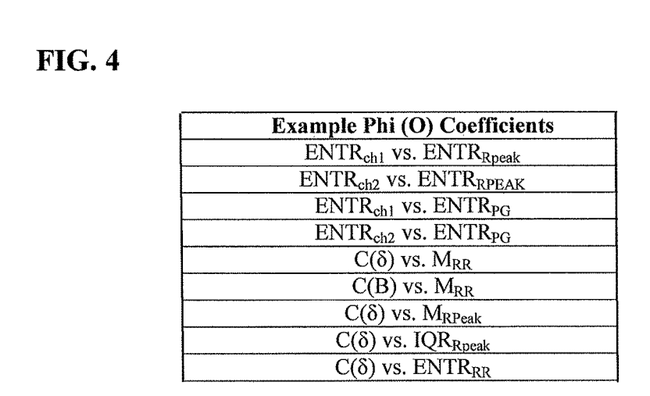
FIG. 4 is a chart of example Phi coefficients derived from different feature values.

Although not specifically discussed in the method illustrated in FIG. 2, alternate embodiments could include similar analysis of recorded respiration data, that is, obtaining feature values of the respiration data, and determining measures of association between the respiration data and the EEG data and/or ECG data. FIG. 1 illustrates how a respiration monitor 5 may be incorporated into the system with leads 14 connected to patient 2. Respiratory data could be generated by any conventional or future developed technique, e.g., plethysmography, a nasal thermocouple, or an oxygen saturation test. FIG. 3C indicates how plethysmography (PG) data would be divided into time segments like the EEG and ECG data (step 60), the entropy of the PG data determined (step 62), and the entropy data binarized (step 61). FIG. 4 suggests an embodiment where the Phi coefficient could be determined between the entropy of the PG data (ENTR$_{PG}$) and the entropy of the various channels of the EEG data.

Similarly, other embodiments might include the above described SUDEP biomarkers together with therapeutic interventions. For example, the system of FIG. 1 may include a stimulation unit 7. The stimulation unit 7 would have a series of electrodes 15 connected to the patient and stimulation unit 7 could, upon instructions from processor 8, deliver a series of electrical signals to the patient's brain that would therapeutically counter-act brain electrical impulses related to seizures. One such stimulation unit is described in published application no. US 2009/0264952, which is incorporated by reference herein in its entirety. Likewise, system 1 may, in combination with or as an alternative to stimulation unit 7, include the drug administration unit 6 which will, upon instructions from processor 8, deliver a therapeutic drug to the patient. One such stimulation unit is described in published application no. US 2012/0298105, which is incorporated by reference herein in its entirety. Still further variations of the invention might utilize different bio-data (i.e., other than PG or ECG) for comparison with EEG data.

Experimental Example—Mouse Model

Mice lacking the Kcna1 gene, which encodes voltage-gated Kv1.1 K+ channels, exhibit severe epilepsy, premature death, and brain-mediated cardiac dysfunction, which make them a useful model of human SUDEP. Kcna1 knockout mice carrying a null allele of the Nav1.2 Na+ channel gene, Scn2a, exhibit about 50% increased survival despite persistent seizures, suggesting that heterozygosity for the Scn2a deletion acts as a protective genetic modifier against SUDEP. It is hypothesized that Scn2a heterozygosity acts as a protective genetic modifier in the Kcna1-null mouse model of SUDEP by altering the association of neural (EEG) with cardiac (ECG) activity, which itself represents a novel biomarker of SUDEP susceptibility.

Age-matched Kcna1−/− and Kcna1−/−; Scn2a+/− mice (n=3/genotype) were implanted with bilateral EEG electrodes overlying the temporal cortex and bilateral thoracic ECG electrodes. Simultaneous EEG-ECG activity was recorded using a DSI monitoring system. For each animal, two EEG signals (1 kHz sampling rate) and one ECG signal (2 kHz sampling rate) were collected for a 18-24 hour period. Each recording was divided into 10 s segments and measures of brain connectivity and heart rate variability were estimated. The following frequency domain measures were estimated from the two EEG signals: Coherence in the δ-band [0.5-3 Hz], θ-band (3.5-7 Hz], α-band (8-12 Hz], β-band [13-20 Hz], and γ-band [21-50 Hz] (C(δ) to C(γ)). From the ECG data, the estimated measures were Median (A), Inter Quartile Range (IQR) and Entropy (ENT) of the R peaks amplitude and the RR intervals duration. The EEG and ECG measures per segment were first binarized (to 0's or 1's depending on their values with respect to their own global medians), and their degree of association over the whole record was then evaluated using the φ coefficient. Statistical significant difference between the φ coefficients of pairs of measures for the two genotypes was assessed with a t-test (a=0.05).

Figure 6A:
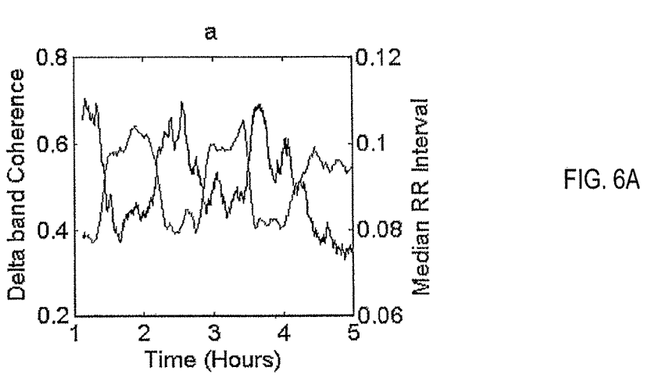
FIGS. 6A and 6B are graphs of results from coherence and median measures over time.
Figure 6B:
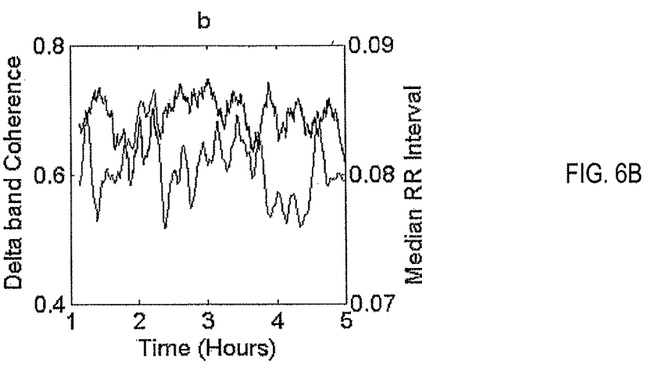

Examples of the measure profiles for one animal from each genotype are given in FIGS. 6A and 6B. C(δ) (EEG) and $M_{RR}$ (ECG) exhibited related behavior over time for the Kcna1−/−; Scn2 a+/− animal (FIG. 6A), whereas for the Kcna1−/− no such relation is evident (FIG. 6B). The average φ coefficients for the two genotypes and pairs of measures that show statistically significant difference are shown in FIG. 7, along with the p-value of the t-test (the rest of the pairs had p-values >0.05). Kcna1−/−; Scn2a+/− mice (lower SUDEP risk) have a statistically significant higher degree of association between neural and cardiac activity than the Kcna1−/− mice (higher SUDEP risk). This reduced association could be indicative of low level of neural control of the heart, which could be a risk factor for SUDEP.

Although the present invention has been described in terms of specific embodiments, those skilled in the art will recognize many obvious modifications and variations. For example, while the above embodiments apply the disclosed methods to SUDEP, these methods may be equally applied to many other sudden death pathologies, e.g., status epilepticus, sudden infant death syndrome, sudden unexpected nocturnal death syndrome, and sudden arrhythmic death syndrome. The methods and systems described herein could be employed as part of a system that includes EEG and ECG data recording devices. Alternatively, the methods and systems could be in the form of software running on a stand-alone device which analyzes EEG/ECG data, estimates SUDEP biomarkers and reports the risk for SUDEP. All such variations and modifications are intended to come within the scope of the following claims.

The invention claimed is:
1. A method for determining an increased risk of death of a patient comprising the steps of:
   a. receiving electrocardiogram (ECG) data of the patient generated during a first time period;
   b. receiving electroencephalogram (EEG) data of the patient generated during the first time period;
   c. composing a feature of the ECG data and a feature of the EEG data over a common time frame, wherein the feature composed from the EEG or ECG data is at least one from the group consisting of mean, standard deviation, Kurtosis, skewness, autoregressive modeling coefficients, Vector autoregressive modeling coefficients, Barlow parameters, Teager energy, Hjorth parameters, Pearson product-moment correlation coefficient, Rank correlation, spectral band power at specific frequencies/frequency bands, normalized spectral band power, spectral edge frequency, median frequency, coherence, directed transfer function, partial coherence, directed coherence, generalized partial directed coherence, Shannon entropy, approximate entropy, sample entropy, spectral entropy, mutual information, transfer entropy, Lyapunov exponents, correlation dimension, recurrence quantification analysis, dynamical entrainment, non-linear interdependence, detrended fluctuation analysis, Hurst exponent, Lempel-Ziv complexity, phase synchronization, phase-amplitude coupling, bispectrum, and bicoherence;
   d. determining a statistical measure of association between features of the ECG data and the EEG data;
   e. determining whether the statistical measure of association exceeds a predetermined threshold, thereby indicating whether the increased risk of death is present;
   f. in response to an indication of the increased risk of death, either (i) delivering a series of electrical signals to therapeutically counter-act brain electrical impulses related to seizures; or (ii) administering a therapeutic drug to the patient; and
   g. wherein the patient suffers from at least one condition from the group consisting of epileptic seizures, status epilepticus, sudden infant death syndrome, sudden unexpected death in epilepsy, and sudden arrythmic death syndrome.

2. The method of claim 1, wherein the first time period is a time period when the patient is not in a seizure state.

3. The method of claim 1, wherein the feature of the EEG data is a coherence between brain recording sites in at least one of the bands from the group consisting of the δ-band, θ-band, α-band, β-band, or the γ-band.

4. The method of claim 3, wherein the feature of the ECG data is at least one of a median (M), an Inter Quartile Range (IQR), or an entropy (ENT) of either R peak amplitudes or length of RR intervals in QRS complexes of the ECG data.

5. The method of claim 4, wherein the feature of the EEG data and the feature of the ECG data are at least one of the pairs $C(δ)$-$M_{Rpeak}$; $C(δ)$-$IQR_{Rpeak}$; $C(δ)$-$ENT_{RR}$; $C(δ)$-$M_{RR}$; or $C(β)$-$M_{RR}$.

6. The method of claim 1, wherein the statistical measure of association is a phi coefficient between the feature of the EEG data and the feature of the ECG data.

7. The method of claim 6, wherein the statistical measure of association threshold is 0.1.

8. The method of claim 1, further comprising the steps of (i) receiving respiratory data of the patient generated during the first time period; (ii) composing a feature of the respiratory data; and (iii) determining a statistical measure of association between the respiratory data and the EEG data and/or the ECG data.

9. The method of claim 1, further comprising the step of, in response to an indication of the increased risk of death, either (i) delivering a series of electrical signals to therapeutically counter-act brain electrical impulses related to seizures; or (ii) administering a therapeutic drug to the patient.

10. A method for treating a patient determined to have an increased risk of death comprising the steps of:
  a. receiving electrocardiogram (ECG) data and electroencephalogram (EEG) data from the patient generated during a first time period when the patient is in an interictal state;
  b. composing a feature of the ECG data and a feature of the EEG data over a common time frame from the first time period and determining a statistical measure of association between the features of ECG data and the EEG data;
  c. determining whether the degree of the statistical measure of association exceeds a predetermined threshold, thereby indicating whether the increased risk of death is present; and
  d. in response to an indication of the increased risk of death, either (i) delivering a series of electromagnetic signals to therapeutically counter-act brain electrical impulses related to seizures; or (ii) administering a therapeutic drug to the patient; and
  e. wherein the patient suffers from at least one condition from the group consisting of epileptic seizures, status epilepticus, sudden infant death syndrome, sudden unexpected death in epilepsy, and sudden arrythmic death syndrome.

11. The method of claim 10, wherein the feature composed from the EEG or ECG data is at least one from the group consisting of mean, standard deviation, Kurtosis, skewness, autoregressive modeling coefficients, Vector autoregressive modeling coefficients, Barlow parameters, Teager energy, Hjorth parameters, Pearson product-moment correlation coefficient, Rank correlation, spectral band power at specific frequencies/frequency bands, normalized spectral band power, spectral edge frequency, median frequency, coherence, directed transfer function, partial coherence, directed coherence, generalized partial directed coherence, Shannon entropy, approximate entropy, sample entropy, spectral entropy, mutual information, transfer entropy, Lyapunov exponents, correlation dimension, recurrence quantification analysis, dynamical entrainment, nonlinear interdependence, detrended fluctuation analysis, Hurst exponent, Lempel-Ziv complexity, phase synchronization, phase-amplitude coupling, bispectrum, and bicoherence.

12. The method of claim 10, wherein the feature of the EEG data is a coherence between brain recording sites in at least one of the bands from the group consisting of the δ-band, θ-band, α-band, β-band, or the γ-band.

13. The method of claim 12, wherein the feature of the ECG data is at least one of a median (M), an Inter Quartile Range (IQR), or an entropy (ENT) of either R peak amplitudes or length of RR intervals in QRS complexes of the ECG data.

14. The method of claim 13, wherein the feature of the EEG data and the feature of the ECG data are at least one of the pairs $C(\delta)$-$M_{Rpeak}$; $C(\delta)$-$IQR_{Rpeak}$; $C(\delta)$-$ENT_{RR}$; $C(\delta)$-$M_{RR}$; or $C(\beta)$-$M_{RR}$.

15. The method of claim 10, wherein the statistical measure of association is a phi coefficient between the feature of the EEG data and the feature of the ECG data.

16. The method of claim 15, wherein the statistical measure of association threshold is 0.1.

* * * * *